(12) United States Patent
Yamakawa et al.

(10) Patent No.: US 6,255,614 B1
(45) Date of Patent: Jul. 3, 2001

(54) SPECIMEN-CONTAINER TRANSFER APPARATUS

(75) Inventors: Nobuyoshi Yamakawa; Hidenari Takaoka; Masanori Nakaya; Toshio Watanabe, all of Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/570,065

(22) Filed: May 12, 2000

(30) Foreign Application Priority Data

May 14, 1999 (JP) .................................................. 11-134942

(51) Int. Cl.[7] ...................................................... B07C 5/00
(52) U.S. Cl. .......................... 209/587; 209/509; 209/522; 209/523; 209/524
(58) Field of Search .................................... 209/509, 522, 209/523, 524, 538, 552, 587, 583, 576, 606, 617

(56) References Cited

U.S. PATENT DOCUMENTS 5,150,795 * 9/1992 Nakayama et al. .................... 209/3.3
6,151,535 * 11/2000 Ehlers ................................... 700/226

* cited by examiner

*Primary Examiner*—Donald P. Walsh
*Assistant Examiner*—Mark Beauchaine
(74) *Attorney, Agent, or Firm*—Shinjyu Intellectual Property Firm

(57) ABSTRACT

An apparatus wherein assayed specimens can be transferred in any order to a specimen-container housing rack automatically and very efficiently, without any restrictions whatsoever on the order in which the specimen containers are placed in the specimen-container racks and assayed, even if different types of specimen vessel are present. This is accomplished in a specimen-container transfer apparatus having: a conveyor unit for transporting specimen-container racks; a specimen-container ID reader for reading the specimen-container identification numbers of the specimen-container racks transported by the conveyor unit; a specimen-container housing-rack table for setting up specimen-container housing racks for housing specimen containers; a specimen-container transfer mechanism for taking specimen containers out of a specimen-container rack and putting them in a specimen-container housing rack; and a control unit for controlling the order in which the specimen containers are put into the specimen-container housing rack.

5 Claims, 6 Drawing Sheets

SPECIMEN-CONTAINER TRANSFER APPARATUS

BACKGROUND OF THE INVENTION

1. Technical Field

The present invention relates to specimen-container transfer apparatuses with which specimen containers containing blood, urine, or other biological samples used in clinical testing are taken out of a specimen-container rack and put into a housing rack in a prescribed order. It is particularly suitable for connection to a conveyance unit that shuttles specimen-container racks between analyzers.

2. Description of Related Art

In clinical testing in hospitals and test centers, various tests such as blood tests, biochemical tests, and general tests are conducted using blood, urine, and other such biological samples. The analyzers used in these tests are generally equipped with a sampler that automatically takes measurements once a specimen-container has been put into the specimen-container rack. Furthermore, conveyor systems that automatically transfer specimen containers between a plurality of analyzers have come to be used in recent years to improve efficiency (see Japanese Laid-Open Patent Applications 63-217274 and 3-94159).

There are times when a specimen-container that has been tested in this way must be re-tested, depending on the test results thereof, the results of other tests, or the like. The specimen containers used in tests are therefore stored for a few days. This is desirable if each specimen-container rack is stored with the specimen containers just as they were when tested, but because specimen-container racks are slender in shape normally for five or ten specimen containers, a place must be prepared for the racks where they will not be tipped over and the order of the specimen containers changed. The standard procedure in testing is to assay specimens in the order they arrive, but this may be interrupted by an emergency specimen-container, or certain special specimen containers may be taken out, so finding the desired specimen-container can be difficult even if they were arranged in order after being measured, and this creates problems in terms of emergency testing, and the like, for facilities that handle large numbers of specimens.

Herein, it is preferable for specimens to be sorted by branch of medicine, in-patient/out-patient, etc., or for them to be rearranged into a suitable order by specimen-container ID numbering. This is manual work, however, and places a tremendous burden on facilities that handle a large number of specimens, which is why it is not actually performed very often.

This work conceivably could be automated by devising a conventional specimen-container conveyor unit by installing behind the analyzer a unit that rearranges into a prescribed order assayed specimen-container racks. But just rearranging the specimen containers in blocks of specimen-container racks will not be very effective unless the specimen containers are also arrayed in the specimen-container rack in the proper order.

SUMMARY OF THE INVENTION

An object of the present invention is to transfer assayed specimens automatically to a specimen-container housing rack in a predetermined order without being restricted in any way by the order in which the specimen containers are set into the specimen-container rack and assayed.

The present invention was conceived in order to achieve the stated object, and provides a specimen-container transfer apparatus equipped with: a conveyance unit for transferring specimen-container racks; a specimen-container ID reader for reading specimen-container identification signals from the specimen-container racks transported by the conveyance unit; a specimen-container housing-rack table on which specimen-container housing racks for housing specimen containers can be set up; specimen-container transfer means for taking specimen containers out of specimen-container racks and putting them into specimen-container housing racks; and a control unit for controlling the order in which the specimen containers are put into the specimen-container housing rack.

From the following detailed description in conjunction with the accompanying drawings, the foregoing and other objects, features, aspects and advantages of the present invention will become readily apparent to those skilled in the art.

DETAILED DESCRIPTION OF THE PREFERRED EMBODIMENTS

"Specimen-containers" used in the specimen-container transfer apparatus of the present invention mean biological samples of blood or urine for example housed in blood sample tubes, spitz tubes, or like vessels. The specimen-container rack is a rack in which these specimen containers are held, and is made to fit a sampling device in specimen analyzers. The transferred specimen-container housing rack is a rack for housing specimen containers, which may be a rack capable of housing many specimen containers (50 or 100 for example), making for convenient storage, or may be the same as the specimen-container rack used in specimen analyzers so as to allow measurement directly in the analyzers. In the present invention, the order in which the specimen containers are placed is not just the order in which the specimen containers are lined up in the rack, but includes their sorting into a plurality of housing racks.

Figure 1:
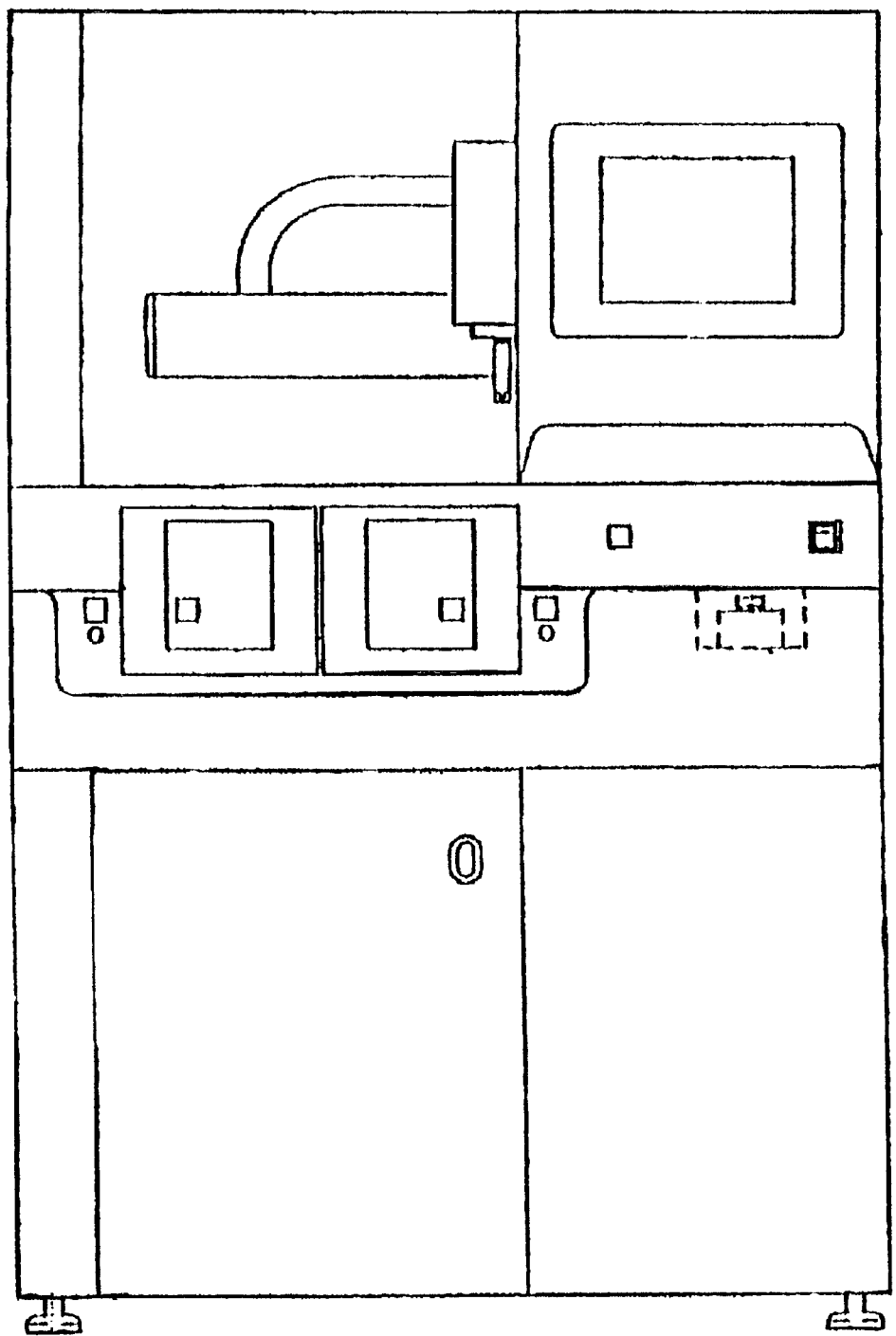
FIG. 1 is a front elevation of a specimen-container transfer apparatus in an embodiment of the present invention.
Figure 2:
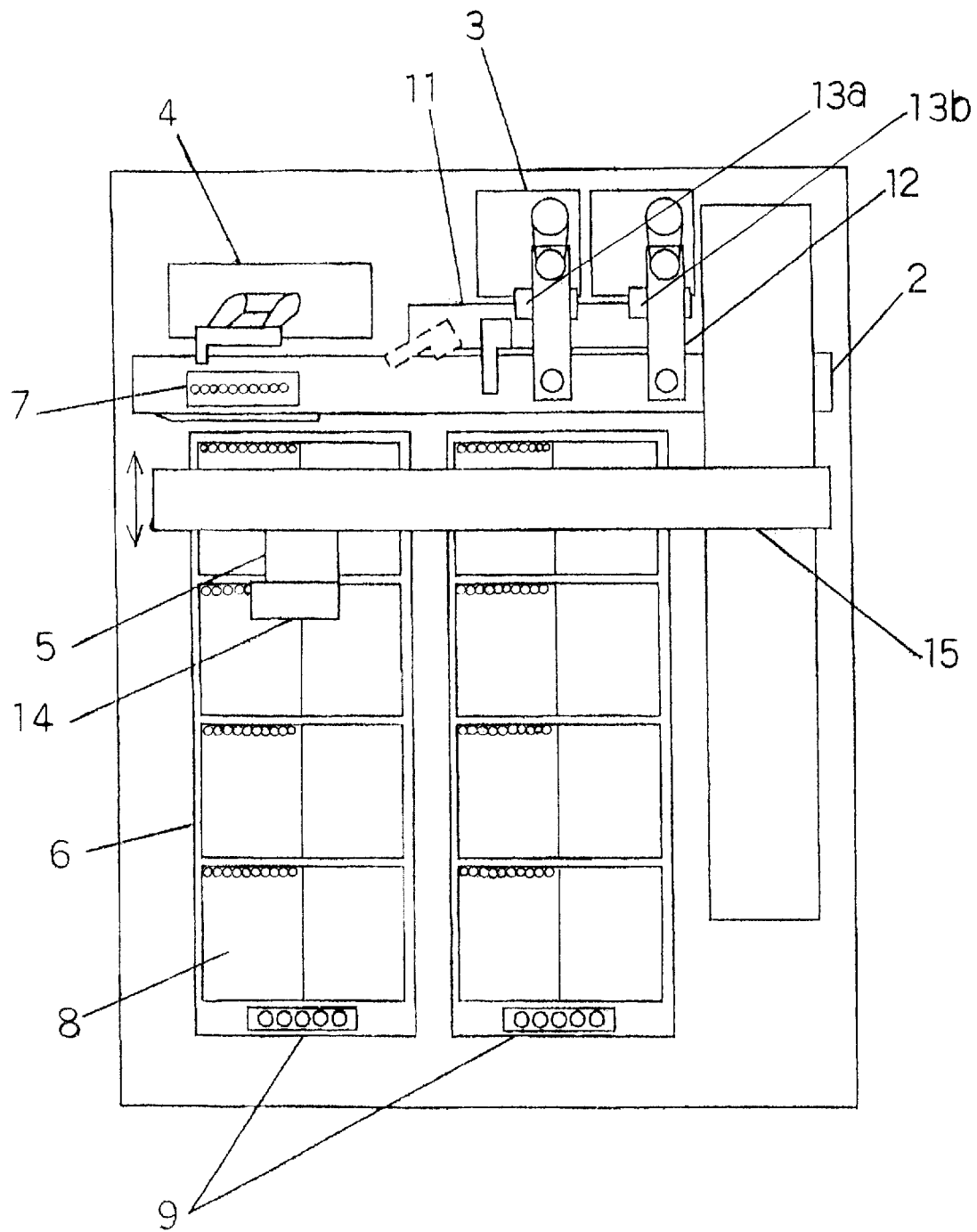
FIG. 2 is a schematic plan view of principal components in the specimen-container transfer apparatus.
Figure 3:
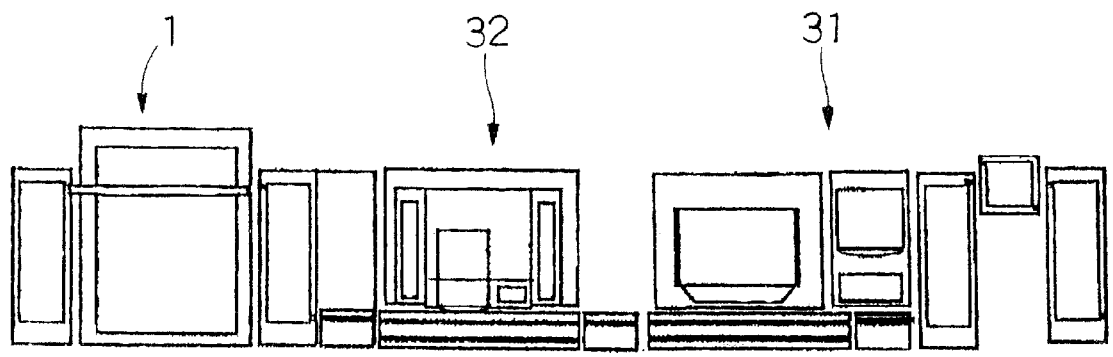
FIG. 3 is an elevational plan of the specimen-container transfer apparatus in connection to a conveyor system between an associated blood analyzer and smear preparation analyzer.

An embodiment of the present invention will now be described through reference to the figures, initially to: FIG. 1, the front view of a specimen-container transfer apparatus 1 in the present embodiment, and FIG. 2, the schematic plan view of the main components of the specimen-container transfer apparatus 1. Further, as shown in FIG. 3, the specimen-container transfer apparatus 1 is connected to the conveyor system of a blood analyzer 31 and a smear preparation analyzer 32, and is controlled by a control unit (not shown). A vacuum blood sample tube filled with a blood sample is used as the specimen-container, and specimen-container racks housing ten specimen containers are transferred by the conveyor system.

The main components comprise: a conveyor unit 2 for transporting specimen-container racks 7 that have been taken in; a specimen-container housing-rack table 6 on which specimen-container housing racks 8 are set up for transferring and housing specimen containers; and a specimen-container transfer section 5 for removing containers set in the specimen-container racks 7 and placing them in the specimen-container housing racks 8.

Figure 4:
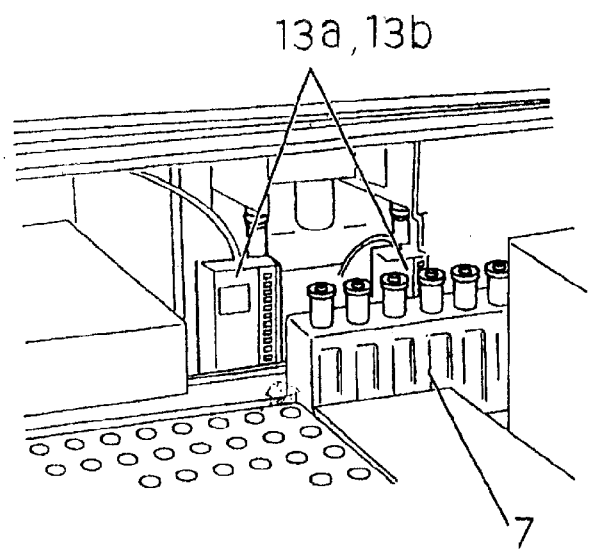
FIG. 4 is an oblique drawing of specimen-container ID readers in the specimen-container transfer apparatus.

The conveyor unit 2 receives a specimen-container rack 7, moves it through the apparatus, and sends it out on the other side, and is designed so that it can be connected with another conveyor unit on either the entry or exit side. The conveyor unit 2 is provided with a specimen-container ID reader 3 and a rack setter 4. The specimen-container ID reader 3 comprises a rack hold-down mechanism 11, and two sets of blood sample tube rotation mechanisms 12 and bar code readers 13a and 13b. FIG. 4 shows the layout of the bar code readers 13a and 13b. The rack hold-down mechanism 11 holds down the specimen-container racks 7 as they move along on the conveyor unit 2, and positions the blood sample tubes in the specimen-container rack in front of the bar code readers 13a and 13b. The rack hold-down mechanism 11 is controlled so that the specimen-container rack 7 is intermittently stopped, for each blood sample tube. The two blood sample tube rotation mechanisms 12 slowly rotate the blood sample tubes around their axes so that they can be read by the bar code readers 13a and 13b no matter which direction the labels affixed to the blood sample tubes in the specimen-container rack are facing. The bar code readers 13 and blood sample tube rotation mechanisms 12 in the two respective sets are configured to enable simultaneous reading, and this allows for efficient reading even if a ten-specimen-container rack is used. The specimen-container ID information read by the bar code readers 13a and 13b is transmitted to the control unit.

The specimen-container rack 7 transferred by the conveyor unit 2 is fixed at a predetermined position by the rack setter 4. In specific terms, the rack setter 4 positions the specimen containers when the specimen-container transfer section 5 removes the blood sample tubes. The rack setter 4 also sets the specimen-container rack into a predetermined position so that the rack will not move as the specimen containers are being removed.

The specimen-container transfer section 5 removes the blood sample tubes from the specimen-container rack 7 and puts them in a specimen-container housing rack 8. Specifically, the specimen-container transfer section 5 has a hand unit 14 for clutching blood sample tubes, and a shifting unit 15 for shifting a clutched blood sample tube. The hand unit 14 comprises a pair of graspers 17 for holding down and clutching blood sample tubes so that even a blood sample tube of a different type can be grasped if mixed in with others, and a base 16 that drives the graspers 17.

Figure 5:
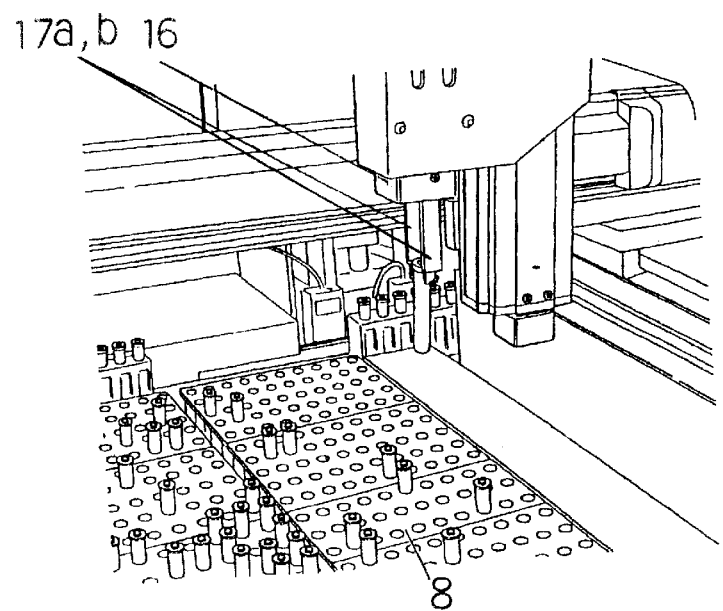
FIG. 5 is an oblique drawing depicting a transfer operation in the apparatus according to the embodiment.
Figure 6:
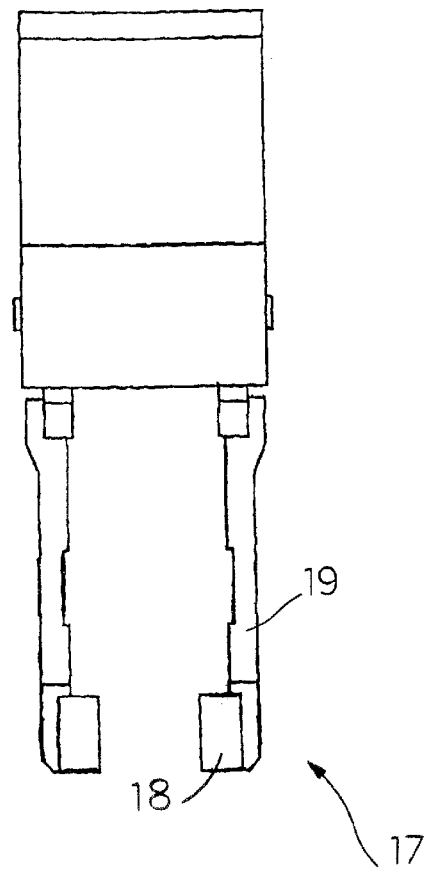
FIG. 6 is a lateral view of a specimen-container grasping device schematically depicted in isolation from the apparatus.
Figure 7:
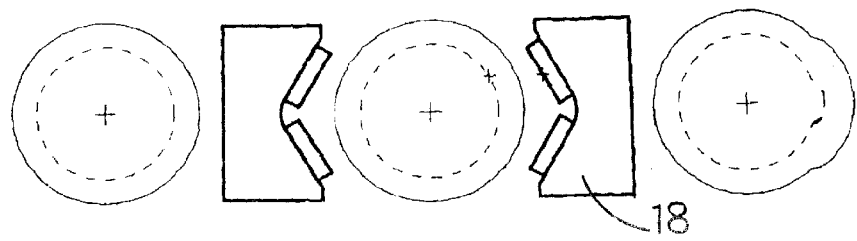
FIG. 7 is an overhead sectional view through grasping hands of the grasping device depicted in FIG. 6, positioned between blood sample tubes.
Figure 8:
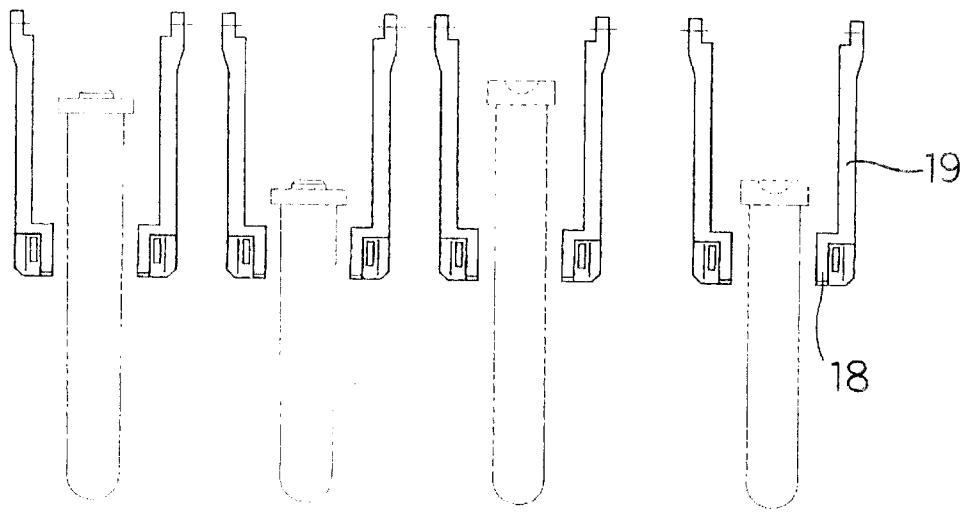
FIG. 8 is a schematic lateral depiction of grasping hands on arms of the FIG. 6 grasping device, in several views shown about to grasp blood sample tubes, depicted in phantom, of different sizes.

Reference is now made to FIG. 5, illustrating an example of the structure of the graspers 17 and the base 16, and to FIG. 6, the side view of the graspers 17. As shown in FIG. 6, the graspers 17 each comprise a grasping hand 18 and a grasping arm 19. As shown in FIG. 7, the inner side of the grasping hands 18 is formed in a concave shape so that a tube from a mixture of blood sample tubes with different diameters ranging from 12 cm (dashed line) up to 15.6 cm (solid line) can be gripped. As shown in FIG. 8, the grasping arms 19 are formed so that even if the length of the blood sample tubes varies, the grasping hands 18 will not hit the caps of the blood sample tubes as long as the grasping hands 18 grip the blood sample tubes at a predetermined height.

Figure 9:
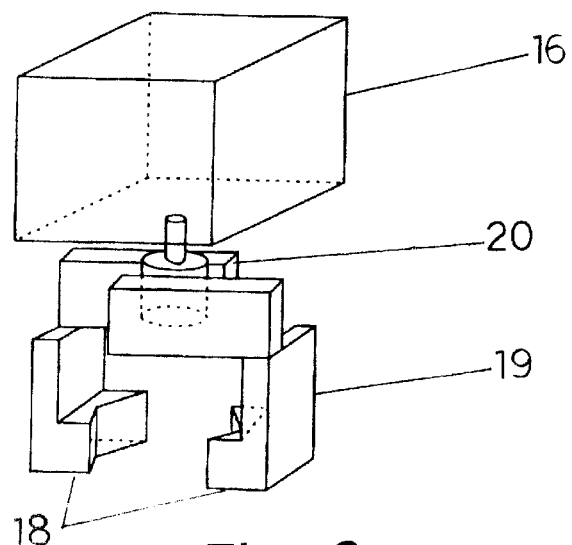
FIG. 9 is a conceptual, oblique depiction of the grasping device with its driving base and drive source.

As diagrammatically depicted in FIG. 9, the base 16 is provided with a drive source that moves the two graspers 17 together and apart so as to grip and release the blood sample tubes. Wherein a servo motor 20 for example is used as the drive source, the servo motor 20 sets the position to which the graspers 17 are moved. If this position is set such that the graspers will close up to a gap that is narrower than the diameter of the blood sample tube, then the servo motor 20 continues drive in an attempt to continue closing the graspers 17 even after they are in contact with the blood sample tube. It is through this action that the graspers 17 are able to keep hold of the blood sample tube. Using this structure allows blood sample tubes of different sizes to be gripped equally well as long as the shape of the graspers 17 accommodates the shape of the blood sample tubes.

An XYZ movement mechanism for vertically and horizontally moving the specimen-container transfer section 5 can be used as the movement mechanism 15 as appropriate, so as to remove blood sample tubes from the specimen-container racks and put them into the specimen-container housing racks.

The specimen-container housing-rack table 6 is used to set up the specimen-container housing racks 8, and in this example eight of the specimen-container housing racks 8 can be set up, each of which is able to hold 50 specimen containers. The specimen-container transfer apparatus 1 is able to discriminate whether the specimen-container housing racks 8 are installed into positions in the specimen-container housing-rack table 6, and to identify the rack ID of a set specimen-container housing rack 8. Holes are provided in five places in specimen-container housing rack 8 set-up positions on the specimen-container housing-rack table 6, and the floors of the specimen-container housing racks 8 are provided with collating pins that differ in presence/absence rack to rack. By recognizing presence/absence of the pins, the specimen-container transfer apparatus 1 according to this configuration is able automatically to recognize whether a specimen-container housing rack has been installed in the set-up sections, and the ID of installed racks.

Figure 10:
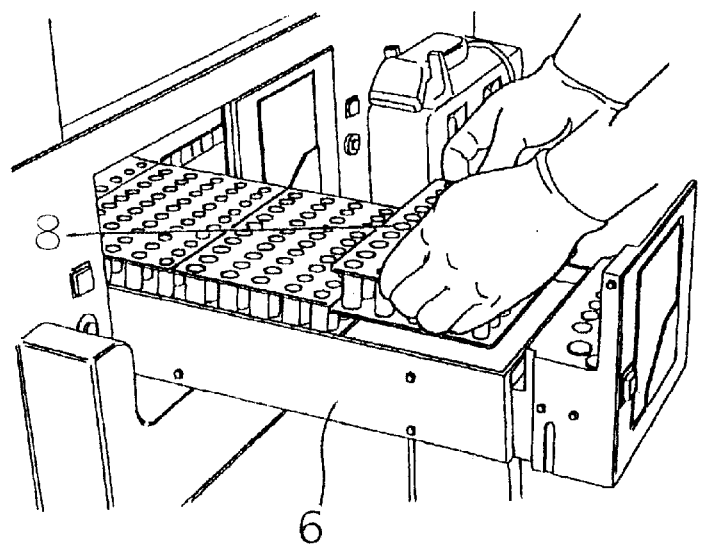
FIG. 10 is an oblique illustration of a opened specimen-container housing-rack table drawer into which specimen-container housing racks are being set up in the specimen-container transfer apparatus.

As shown in FIG. 10, the specimen-container housing-rack table 6 is designed such that it is taken out by being pulled from the front of the apparatus housing. The user presses a pause button when he wants to remove a specimen-container housing rack 8 during specimen-container transfer. The apparatus then halts the transfer at a good stopping point, and issues a message that the specimen-container housing-rack table 6 can be pulled out. The user is able to replace a specimen-container housing rack 8 by pulling out the specimen-container housing-rack table 6.

Figure 11:
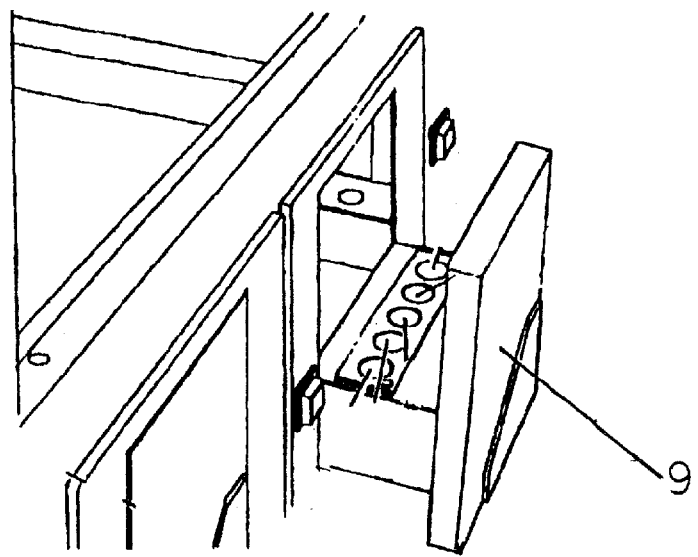
FIG. 11 is an oblique illustration of a manual specimen-container-housing drawer shown opened in the specimen-container transfer apparatus.

A manual operation rack 9 capable of housing specimen containers is provided in front of the specimen-container housing-rack table 6, separately from this specimen-container housing-rack table 6. As shown in FIG. 11, this manual operation rack 9 is designed so that just the manual operation rack 9 can be pulled out from the front and 20 specimen containers can be taken out or put in independently of the specimen-container housing-rack table 6. Using this manual operation rack 9 allows specimen containers to be taken out or put in without halting the specimen-container transfer operation.

The process by which this apparatus arranges the blood sample tubes in the specimen-container racks 7 will now be described. Specimens that have already been assayed by the analyzer are conveyed by specimen-container rack 7 from another conveyor component to the specimen-container transfer apparatus 1. This specimen-container rack 7 is received by the conveyor unit 2 and first conveyed to the specimen-container ID reader 3. At the specimen-container ID reader 3 the rack hold-down mechanism 11 stops the ten-specimen-container specimen rack 7 and positions it so that the first and sixth blood sample tubes in the specimen-container rack 7 are in front of the bar code readers 13a and 13b. The blood sample tube rotation mechanisms 12 then descend over the respective blood sample tubes, and hold down the blood sample tubes from above while slowly rotating them. During this time the bar code readers 13a and 13b read the bar codes affixed to the rotating blood sample tubes. Once the reading of the blood sample tubes is complete, the blood sample tube rotation mechanisms 12 rise up and away from the blood sample tubes. The rack hold-down mechanism 11 then moves the specimen-container rack 7 the distance between blood sample tubes and positions the second and seventh blood sample tubes in front of the bar code readers 13a and 13b. The reading of the blood sample tubes continues in this fashion until the bar codes of all the blood sample tubes in the specimen-container rack 7 have been read, at which point the rack hold-down mechanism 11 releases the specimen-container rack 7.

Next, the specimen-container rack 7 is transferred by the conveyor unit 2 to the specimen-container rack setter 4. The specimen-container rack setter 4 sets the specimen-container rack 7 into a predetermined position. The specimen-container transfer section 5 then shifts into the blood sample tube position set by the specimen-container rack setter 4. The hand unit 14 descends to a predetermined height with the graspers 17a and 17b open, and then closes the graspers 17a and 17b to grip a blood sample tube. The hand unit 14 rises while still gripping the blood sample tube, and the blood sample tube is removed from the specimen-container rack 7 set by the specimen-container rack setter 4. Then, while clutching the blood sample tubes, the specimen-container transfer section 5 is shifted by the shifting unit 15 to a predetermined position on the specimen-container housing-rack table 6 according to instructions from a host with regard to read-out specimen-container IDs. The hand unit 14 descends to a predetermined height while still grasping the blood sample tube, and houses the blood sample tube in the housing rack 8 on specimen-container housing-rack table 6. The graspers 17a and 17b of the hand unit 14 are opened, the blood sample tube is released, and the hand unit 14 rises.

This transfer of blood sample tubes is repeated until all of the blood sample tubes in the specimen-container rack have been transferred, whereupon the specimen-container rack 7 is released from the specimen-container rack setter 4 and sent out by the conveyor unit 2. It is then sent to another conveyor apparatus or specimen-container rack housing unit connected to a (not shown) send-out section.

The specimen-container transfer apparatus of the present invention is equipped with a mechanism for housing specimen-container racks 7, separate from the specimen-container ID reader 3 and the specimen-container rack setter 4, while a single conveyor unit 2 is constantly moving. This structure allows specimen-container ID reading and specimen-container transfer to be carried out simultaneously, while affording a degree of freedom in the control of the specimen-container rack 7, and allows specimen-container transfer to be carried out more efficiently.

The order in which the specimen containers are housed into the rack can be set as desired with the control unit, according to the procedures of the facility in question. For instance, specimens can be sorted by clinical department, such as internal medicine or obstetrics, or by in-patient and out-patient, or by the geographical region where the specimens were collected in the case of a testing center, or by specimen-container ID or patient ID.

The specimen containers can also be arrayed on the basis of assay results from the analyzer. For instance, if the measurement results do not fall within the normal range for a particular category, then those specimen containers can be put in a separate rack for re-testing. The measurement results can also be sorted into a number of levels, such as negative, weakly positive, and strongly positive, and the specimen-container housing racks can be sorted by level and arranged in a specific order. Furthermore, the specimen containers can be arranged using not only the measurement results from the analyzer of the conveyor system, but also any desired clinical information inputted to the host computer of the facility. For example, the arrangement sequence can be set on the basis of the difference from previous test result values, physician findings, or other test results.

As to the operation of the manual operation rack 9, as mentioned above, this manual operation rack 9 is designed so that just the manual operation rack 9 can be pulled out from the front and specimen containers can be taken out or put in independently of the specimen-container housing-rack table 6. The specimen containers to be taken out can be designated by specimen-container ID, or can be selected using the measurement results from the analyzer. Examples include specimens with a measurement error, and those whose measurement results exceed the set range. These specimen containers are moved by the specimen-container transfer means 5 from the specimen-container rack 7 directly into the manual operation rack 9, or into the manual operation rack 9 after being held in a specimen-container housing rack S. The specimen containers thus moved can be taken out by pulling open just the manual operation rack 9, even if the transfer work is in progress.

Also, any specimen containers whose ID could not be read can be designated and taken out of the manual operation rack 9, and their ID read once again by a hand-held scanner 21 connected to the apparatus. If a bar code is so badly damaged that the specimen-container ID cannot be read even with the hand-held scanner 21, then the specimen-container ID is inputted manually. Once the input of the specimen-container ID is complete, that blood sample tube is put back into the manual operation rack 9, and an instruction is issued to move the tube to the position in the specimen-container housing rack 8 according to this specimen-container ID. The specimen-container transfer section 5 transfers the blood sample tube in the manual operation rack 9 to the specimen-container housing rack 8 corresponding to the specimen-container ID according to this instruction. Similarly, any blood sample tubes that did not pass through the specimen-container conveyor unit can be transferred in a predetermined order from the manual operation rack 9 to the specimen-container housing rack 8.

Putting the desired specimen-container housing racks on reserve status can enhance operational performance. For instance, specimen containers whose ID could not be read by the specimen-container ID reader 3 are put in a specimen-container housing rack designated as reserve. Also, if an installed specimen-container housing rack 8 should become full of blood sample tubes and has no room for more, any further specimen containers may temporarily be put in a specimen-container housing rack 8 designated as reserve. When this designated specimen-container housing rack 8 is replaced with an empty rack, the specimen containers are transferred to this rack. This allows the transfer process to continue uninterrupted even if the designated specimen-container housing racks 8 become full.

With the specimen-container transfer apparatus of the present invention, assayed specimens can be transferred in the proper order to a specimen-container housing rack automatically and very efficiently, without any restrictions whatsoever on the order in which the specimen containers are placed in the specimen-container racks and assayed, even if different types of specimen-container vessel are present. It is also possible for these specimen containers to be rearranged and held in an order based on data such as the measurement results of an analyzer.

While only selected embodiments have been chosen to illustrate the present invention, to those skilled in the art it will be apparent from this disclosure that various changes and modifications can be made herein without departing from the scope of the invention as defined in the appended claims. Furthermore, the foregoing description of the embodiments according to the present invention is provided for illustration only, and not for the purpose of limiting the invention as defined by the appended claims and their equivalents.

What is claimed is:

1. A specimen-container transfer apparatus, comprising:
   a conveyor unit for transporting specimen-container racks;
   a specimen-container ID reader for reading specimen-container identification numbers from the specimen-container racks transported by said conveyor unit;
   a specimen-container housing-rack table for setting up specimen-container housing racks for housing specimen containers;
   specimen-container transfer means for taking specimen containers out of specimen-container racks and putting them in order into specimen-container housing racks; and
   a control unit associated with said specimen-container transfer means for controlling the order in which specimen containers are put into the specimen-container housing rack by said specimen-container transfer means.

2. The specimen-container transfer apparatus set forth in claim 1, wherein said conveyor unit comprises a specimen-container-rack setting unit for setting specimen-container racks into a predetermined position and removing specimen containers from the specimen-container racks.

3. The specimen-container transfer apparatus set forth in claim 1, wherein a secondary specimen-container housing section for housing specimen containers is provided separately from the specimen-container housing-rack table, said secondary specimen-container housing section being configured for putting in and out specimen containers independently from the specimen-container housing-rack table.

4. The specimen-container transfer apparatus set forth in claim 1, said specimen-container transfer means comprising a plurality of grasping hands having concave-shaped inner sides, wherein the specimen-container transfer apparatus includes a servo motor for driving said grasping hands to grasp and to release specimen containers.

5. The specimen-container transfer apparatus set forth in claim 1, being associated with at least one specimen analyzer, wherein the order in which specimen containers are put into the specimen-container housing rack is established based on analysis result information received from the analyzer and inputted to the control unit.

* * * * *